United States Patent [19]

Kinney et al.

[11] Patent Number: 5,021,569

[45] Date of Patent: Jun. 4, 1991

[54] 4-AZATRICYCLO[4.3.1.1(3,8)]UN-DECYLARYLPIPERAZINES WITH ANXIOLYTIC ACTIVITY

[75] Inventors: William A. Kinney, Churchville, Pa.; Nancy E. Lee, Attleboro, Mass.

[73] Assignee: American Home Products Corporation, New York, N.Y.

[21] Appl. No.: 537,188

[22] Filed: Jun. 12, 1990

[51] Int. Cl.5 ............................................. C07D 403/14
[52] U.S. Cl. ..................................................... 540/581
[58] Field of Search ........................................... 540/581

[56] References Cited

U.S. PATENT DOCUMENTS

| | | | |
|---|---|---|---|
| 4,557,865 | 12/1985 | Georgiev et al. | 540/581 |
| 4,636,563 | 1/1987 | Abou-Gharbia | 544/405 |
| 4,797,489 | 1/1989 | Abou-Gharbia et al. | 544/331 |
| 4,818,756 | 4/1989 | Seidel et al. | 544/94 |
| 4,855,430 | 8/1989 | Abou-Gharbia et al. | 544/364 |
| 4,873,331 | 10/1989 | Childers, Jr. et al. | 544/295 |

*Primary Examiner*—Cecilia Shen
*Attorney, Agent, or Firm*—Walter Patton

[57] ABSTRACT

4-Azatricyclo[4.3.1.1(3,8)]undecylarylpiperazine compounds of this invention demonstrated affinity for the 5-hydroxytryptamine-1A receptor site (5-HT$_{1A}$) and to a lesser extent, for dopamine-2 receptor sites (D$_2$). Compounds with such a profile provide a treatment for CNS disorders such as anxiety, depression, and sexual disturbances without EPS liability.

7 Claims, No Drawings

4-AZATRICYCLO[4.3.1.1(3,8)]UNDECYLARYLPIPERAZINES WITH ANXIOLYTIC ACTIVITY

BACKGROUND OF INVENTION

Recent research has provided a growing body of literature which attributes the activity of some of the newer classes of CNS agents to their selective activation of the serotonin receptor subtype designated the 5-HT$_{1A}$ receptor. This has been the case especially for compounds such as buspirone (8-[4-[-4-(2-pyrimidinyl)-1-piperazinyl]butyl]-8-azaspiro[4.5]decane-7,9-dione) and TVX Q 7821 (2-[4-[4-(2-pyrimidinyl)-1-piperazinyl]buyl]-1,2-benzisothiazol-3-(2H)one-1,1-dioxide hydrochloride). See Eison et al., *Pharmacol. Biochem. and Behav.*, 24, 701 (1986); Dompert et al., *Naunyn-Schmiedeberg Arch. Pharmacol.*, 328, 467 (1985) and Spencer and Traber, *Psychopharmacol.*, 91, 25 (1987). Both of the compounds cited above are anxiolytics which demonstrate binding at the 5-HT$_{1A}$ site, while other classic anxiolytics, such as the benzodiazepines and pentobarbital, do not act via the 5-HT$_{1A}$ receptor. Moreover, compounds such as TVX Q 7821 have been found to possess antidepressant activity (see U.S. Pat. No. 4,818,756) while buspirone has been found to be useful in the treatment of sexual dysfunction (see U.S. Pat. No. 4,640,921 (1987)).

Dopamine is known to play a major role in the nigrostriatal pathway for controlling extrapyramidal motor function. Blockade of these receptors by a nonselective potent D$_2$-antagonist results in various EPS effects. Compounds used for anxiety with low affinity for D$_2$-receptors will be devoid of EPS liability (AbouGharbia, U.S. Pat. No. 4,636,563 (1987)).

Compounds of this invention demonstrated affinity for the 5-hydroxytryptamine-1A receptor site (5HT$_{1A}$) and to a lesser extent, for dopamine-2 receptor sites (D$_2$). Compounds with such a profile provide a treatment for disorders such as anxiety, depression, and sexual disturbances without EPS liability.

PRIOR ART

The polycyclic amines of U.S. Pat. No. 4,855,430 (1989) have the structure:

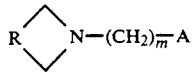

(R, A and m are as defined therein).

The compounds of the present invention contain a polycyclic amine unit with only one methylene spacer between the nitrogen and the tertiary carbon of the polycycle, whereas the previous invention contains two methylene spacers. Furthermore, the present invention contains a 4-azahomoadamantane polycyclic unit, which is dissimilar to polycyclic units used in U.S. Pat. No. 4,855,430 (1989).

U.S. Pat. No. 4,797,489 (1989) and U.S. Pat. No. 4,873,331 (1989) reveal adamantyl and noradamantyl esters respectively, but there are no examples containing an azaadamantane or azahomoadamantane.

In U.S. Pat. No. 4,557,865 (1985) compounds are claimed that have activity against influenza A and type Z herpes virus. They claim N-substituted 7-azatricyclo[4.3.1.1(3,8)]undecanes, substituted by H, substituted benzyl, unsubstituted benzyl, cinnamoyl, etc., but none of the examples contains arylpiperazines nor do they claim CNS activity for their compounds.

SUMMARY OF THE INVENTION

This invention relates to novel compounds having CNS activity and being characterized by the general formula (I):

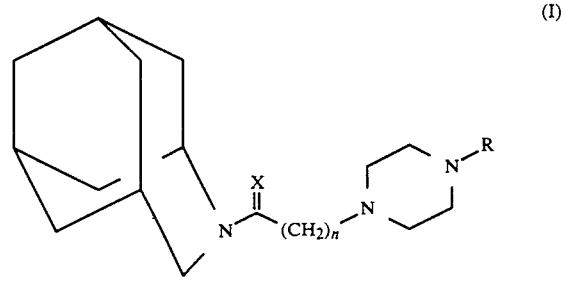

wherein R is unsubstituted or substituted phenyl, benzyl, pyridinyl, pyrimidinyl, or pyrazinyl, where the substituents are selected from the group consisting of lower alkyl containing 1 to 6 carbon atoms, lower alkoxy containing 1 to 6 carbon atoms, halo, cyano, nitro, and perhalomethyl; X is O or H$_2$; n is 1 to 4 and the pharmaceutically acceptable salts thereof.

A preferred aspect of the present invention are the compounds of formula (I) wherein R is substituted phenyl wherein the substituents are selected from the group consisting of methoxy or halogen or R is pyrimidinyl; X is O or H$_2$; n is 2 and the pharmaceutically acceptable salts thereof.

A still further preferred aspect of the present invention are the compounds
1-(4-azatricyclo[4.3.1.1(3,8)]undec-4-yl)-3-[4-(3-chlorophenyl)-1-piperazinyl]-1-propanone;
4-[3-[4-(3-chlorophenyl)-1-piperazinyl]propyl]-4-azatricyclo[4.3.1.1(3,8)]undecane;
1-(4-azatricyclo[4.3.1.1(3,8)]undec-4-yl)-3-[4-(2-methoxyphenyl)-1-piperazinyl]-1-propanone;
4-[3-[4-(2-methoxyphenyl)-1-piperazinyl]propyl]-4-azatricyclo[4.3.1.1(3,8)]undecane;
1-(4-azatricyclo[4.3.1.1(3,8)undec-4-yl)-3-[4-(2-pyrimidinyl)-1-piperazinyl]-1-propanone;
and the pharmaceutically acceptable salts thereof.

Acid addition salts of the above-identified compounds also fall within the present invention. The acids which are used to form addition salts include inorganic acids such as hydrochloric, hydrobromic, sulfuric, phosphoric and nitric acid as well as organic acids such as acetic, succcinic, adipic, propionic, tartaric, fumaric, maleic, oxalic, citric, benzoic, toluenesulfonic and methanesulfonic acid.

Compounds of the present invention may be prepared via a variety of routes using conventional methods and commercially available starting materials. For example, 4-azahomoadamantane, available from adamantanone by the procedure of Narayanan and Setescak (J. Heterocycl. Chem., 6(3), 445–6 (1969)), was reacted with 3-bromopropionyl chloride in the presence of a base such as diisopropylethylamine to yield the bromoamide (II). Arylpiperazines were treated with (II) in the presence of a base such as diisopropylethylamine to prepare the desired compounds of this invention (I), wherein X is O. The compounds of this invention (I), wherein X is H$_2$ were available by reduction with diborane, followed by treatment with hydrochloric acid in refluxing methanol.

SCHEME 1

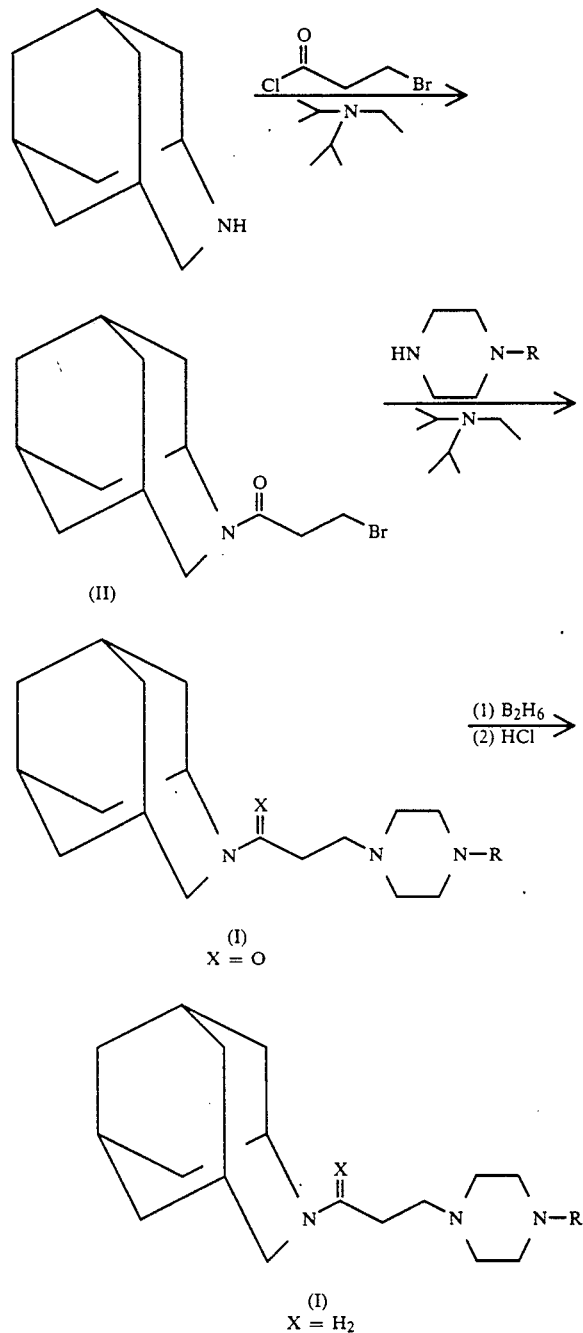

The following examples demonstrate the preparation and pharmacological testing results of compounds within the scope of this invention.

EXAMPLE 1

1-(4-Azatricyclo[4.3.1.1(3,8)]undec-4-yl)-3-[4-(3-chlorophenyl)-1-piperazinyl]-1-propanone Step (1) Preparation of 1-(4-Azatricyclo[4.3.1.1(3,8-)]undec-4-yl)-3-bromo-1-propanone A solution of 4-azatricyclo[4.3.1.1(3,8)]undecane (7.5 g, 50 mmol) in dichloromethane (250 mL) was treated with 3-bromopropionyl chloride (8.5 g, 50 mmol).

Diisopropylethylamine (8.7 mL, 50 mmol) was introduced and the reaction mixture was poured into water (500 mL) after one hour at room temperature. The aqueous layer was extracted with dichloromethane (3×200 mL) and the combined organic material was dried and concentrated to give a crude oil, which was purified by flash chromatography (13 cm diameter, elution with 40% ethyl acetate in petroleum ether) to afford a colorless semi-solid (11.8 g, 82%).

$^1$H NMR (CDCl$_3$, 400 MHz): δ 5.09 (m, 0.6H), 4.14 (m, 0.4 H), 3.65 (t,J=7Hz, 2H), 3.58 (d,J=4Hz, 0.8H), 3.50 (d,J=4Hz, 1.2H), 2.94 (t,J=7Hz, 0.8H), 2.89 (t, J=7Hz, 1.2H), 2.25 (m, 1H), 2.0-1.9 (m, 6H), 1.6-1.5 (m, 6H).

IR: (KBr, cm$^{-1}$): 1640, 1430.

MS (EI): 287 (M+,4), 285 (M+,4), 206(100).

Step (2) Preparation of 1-(4-Azatricyclo[4.3.1.1(3,8-)]undec-4-yl)-3-[4-(3-chlorophenyl)-1-piperazinyl]-1-propanone A solution of 1-(4-azatricyclo[4.3.1.1(3,8)]undec-4-yl)-3-bromo-1-propanone (1.96 g, 6.8 mmol), 1-(3-chlorophenyl)piperazine hydrochloride (1.60 g, 6.8 mmol) and diisopropylethylamine (2.4 mL, 14 mmol) in anhydrous dimethylformamide (100 mL) was heated at 60° C. for 19 hours. The reaction mixture was poured into water (700 mL) and extracted with ethyl acetate (2×200 mL). The combined organic layers were dried, preadsorbed onto silica gel, and purified by flash chromatography (8 cm diameter, gradient elution with 2-5% methanol in dichloromethane). The resulting solid was recrystallized from ethyl acetate in hexane to yield a light tan solid (1.4 g, 51%, m.p. 110°-112° C.).

$^1$H NMR (CDCl$_3$, 400 MHz): δ 7.16 (t,J=8Hz, 1H), 6.87 (t, J=2Hz, 1H), 6.79 (m, 2H), 5.12 (m, 0.6H), 4.25 (m, 0.4H), 3.61 (d, J=4Hz, 0.8H), 3.55 (d, J=4Hz, 1.2H), 3.20 (m, 4H), 2.80 (m, 2H), 2.65 (m, 4H), 2.59 (m, 2H), 2.27 (m, 1H), 2.0-1.9 (m, 6H), 1.65-1.5 (m, 6H)

IR(KBr,cm$^{-1}$): 1630, 1590.

MS (FAB): 402 (MH+,52), 217 (32), 109 (30), 91 (100).

Anal. Calcd. for C$_{23}$H$_{32}$ClN$_3$O: C, 68.72; H, 8.02; N, 10.45. Found: C, 68.41; H, 8.12; N, 10.26.

EXAMPLE 2

4-[3-[4-(3-Chlorophenyl)-1-piperazinyl]propyl]-4-azatricyclo[4.3.1.1(3,8)]undecane Dihydrochloride One Third Hydrate A solution of 1-(4-azatricyclo[4.3.1.1(3,8)]undec-4-yl)-3-[4-(3-chlorophenyl)-1-piperazinyl]-1-propanone (700 mg, 1.74 mmol) in anhydrous tetrahydrofuran (70 mL) under nitrogen was treated with 1M borane in tetrahydrofuran (8.7 mL, 8.7 mmol). The reaction mixture was heated to reflux for 20 hours, cooled in an ice bath, quenched with 6N hydrochloric acid (40 mL), and evaporated. The aqueous residue was made basic with 2.5N sodium hydroxide solution, extracted with ethyl acetate (2×100 ML), and concentrated. The residue was dissolved in methanol (60 mL) and 6 N hydrochloric acid solution (40 mL) and heated to reflux for 20 hours. The solution was neutralized with 2.5N sodium hydroxide solution and the methanol was removed. The aqueous material was extracted with ethyl acetate (2×100 mL), which was dried and evaporated. The residue was dissolved in ether, treated with ethereal hydrogen chloride, evaporated, and recrystallized from methanol in ethyl acetate to afford a white solid (430 mg, 53%, m.p. 280°-283° C. (dec.)).

¹NMR (DMSO, 400 MHz): δ 11.11 (br s, NH), 10.48 (br s, NH), 7.26 (t, J=8Hz, 1H), 7.05 (br s, 1H), 6.96 (br d, J=8Hz, 1H), 6.86 (br d, J=8Hz, 1H), 3.88 (d, J=13Hz, 2H), 3.72 (br s, 1H), 3.58 (m, 3H), 3.4–3.0 (m, 9H), 2.4–2.2 (m, 4H), 2.0–1.8 (m, 8H), 1.7–1.5 (m, 3H).

MS (FAB) 388 (MH+, 28), 217 (25), 109 (28), 91 (100), 79 (28).

Anal. Calcd. for $C_{23}H_{36}Cl_3N_3 \cdot \frac{1}{4}H_2O$: C, 59.16; H, 7.92; N, 9.00. Found: C, 59.35; H, 7.88; N, 8.92.

EXAMPLE 3

1-(4-Azatricyclo[4.3.1.1(3,8)]undec-4-yl)-3-[4-(2-methoxyphenyl)-1-piperazinyl]-1-propanone Dihydrochloride Hydrate A solution of 1-(4-azatricyclo[4.3.1.1(3,8)]undec-4-yl)-3-bromo-1-propanone (1.99 g, 6.96 mmol), 1-(2-methoxyphenyl)piperazine hydrochloride (1.59 g, 6.95 mmol), and diisopropylethylamine (2.4 mL, 14 mmol) in anhydrous dimethylformamide (100 mL) was heated at 60° C. for 24 hours. The reaction mixture was poured into water (700 mL) and extracted with ethyl acetate (2×200 mL). The combined organic layers were dried, preadsorbed into silica gel, and purified by flash chromatography (8 cm diameter, elution with 2% methanol in dichloromethane). The resulting oil (1.6 g) was dissolved in ether, treated with ethereal hydrogen chloride, and evaporated. Recrystallization from methanol in hexane afforded a white solid (600 mg, 18%, m.p. 215°–217° C.).

¹H NMR (DMSO, 400 MHz): δ 10.9 (br s, NH), 7.0–6.9 (m, 4H), 4.95 (br s, 0.6H), 4.25 (br s, 0.4H), 3.79 (s, 3H), 3.6–2.9 (m, 14H), 2.25 (br s, 1H), 2.0–1.8 (m, 6H), 1.6–1.4 (m, 6H).

IR (KBr, cm⁻¹): 1620.

MS (EI): 397 (M+, 2.5), 191 (30), 189 (27), 150 (46), 147 (100).

Anal. Calcd. for $C_{24}H_{39}Cl_2N_3O_3$: C, 59.01; H, 8.05; N, 8.60. Found: C, 59.17; H, 7.80; N, 8.61.

EXAMPLE 4

4-[3-[4-(2-Methoxyphenyl)-1-piperazinyl]propyl]-4-azatricyclo[4.3.1.1(3,8)]undecane Trihydrochloride One Quarter Hydrate A solution of 1-(4-azatricyclo[4.3.1.1(3,8)]undec-4-yl)-3-[4-(2-methoxphenyl)-1-piperazinyl]-1-propanone (1.0 g, 2.5 mmol) in anhydrous tetrahydrofuran (100 mL) under nitrogen was treated with 1M borane in tetrahydrofuran (12.5 mL, 12.5 mmol) and heated at reflux temperature for 20 hours. The reaction mixture was cooled in an ice bath and quenched with 6N hydrochloric acid solution (40 mL). After evaporation the aqueous material was made basic with 2.5N sodium hydroxide solution and extracted with ethyl acetate (2×100 mL), which was concentrated. The resultant oil was dissolved in methanol (60 mL) and 6N hydrochloric acid solution (40 mL) and heated to reflux for 20 hours. The solution was neutralized with 2.5N sodium hydroxide solution and the methanol was removed. The aqueous material was extracted with ethyl acetate, which was dried and evaporated. The residue was dissolved in ether, treated with ethereal hydrogen chloride, and recrystallized from methanol in ethyl acetate to yield a white solid (600 mg, 48%, m.p. 275°–277° C. (dec.)).

¹H NMR (DMSO, 400 MHz): δ 11.3 (br s, NH), 10.7 (br s, NH), 7.0–6.9 (m, 4H), 3.79 (s, 3H), 3.7–3.0 (m, 15 H), 2.4–2.2 (m, 4H), 2.0–1.8 (m, 8H), 1.7–1.5 (m, 3H).

MS (FAB): 384(MH+, 15), 217 (30), 109 (28), 91 (100).

Anal. Calcd. for $C_{24}H_{40}Cl_3N_3O \cdot \frac{1}{4}H_2O$: C, 57.95; H, 8.21; N, 8.45. Found: C, 58.18; H, 8.17; N, 8.44.

EXAMPLE 5

1-(4-Azatricyclo[4.3.1.1(3,8)]undec-4-yl)-3-[4-(2-pyrimidinyl)-1-piperazinyl]-1-propanone A solution of 1-(4-azatricyclo[4.3.1.1(3,8)]undec-4-yl)-3-bromo-1-propanone (2.00 g, 6.99 mmol), 1-(2-pyrimidinyl)piperazine dihydrochloride (1.66 g, 7.00 mmol), diisopropylethylamine (3.6 mL, 21 mmol) in anhydrous dimethylformamide (100 mL) was heated at 60° C. for 23 hours. The reaction mixture was poured into water (700 mL) and extracted with ethyl acetate (2×200 mL). The combined organic layers were dried, preadsorbed into silica gel, and purified by flash chromatography (8 cm diameter, elution with 2.5% methanol in dichloromethane). The resulting solid was stirred over hexane for 2 hours and filtered to yield a beige solid (800 mg, 31%, m.p. 117°–119° C.).

¹H NMR (DMSO, 400 MHz): δ 8.33 (d, J=4.5Hz, 2 H), 6.60 (t, J=4.5 Hz, 1H), 4.92 (m, 0.6 H), 4.28 (m, 0.4 H), 3.69 (m, 4H), 3.54 (d, J=4 Hz, 1.2 H), 3.43 (d, J=4Hz, 0.8 H), 2.6–2.5 (m, 4 H), 2.43 (m, 4 H), 2.21 (m, 1 H), 2.0–1.8 (m, 6 H), 1.6–1.4 (m, 6 H).

IR (KBr, cm⁻¹): 1630, 1590.

MS (FAB): 370 (MH+, 100), 217 (56), 177 (22), 131 (24), 109 (44).

Anal. Calcd. for $C_{21}H_{31}N_5O$: C, 68.26; H, 8.46; N, 18.95. Found: C, 67.88; H, 8.64; N, 18.68.

The compounds of this invention are antidepressant, anxiolytic agents useful in the treatment of depression and/or anxiety as a singular, primary mental problem as well as secondary, attending problems such as sexual dysfunction. Compounds of this invention lack EPS liability as is demonstrated by weak affinity for the $D_2$ receptor.

The $D_2$ receptor affinity of compounds of this invention was determined by a modification of the test procedure of Fields et al., Brain Res. 136, 578 (1977) and Yamamura et al., eds., Neurotransmitter Receptor Binding, Raven Press, N.Y. (1978) as discussed in U.S. Pat. No. 4,636,563 (1987). The percentage reduction of ³H-spiroperidol binding at 1 μM concentration of test compound is reported, infra. Buspirone exhibits a $K_i$ value of 78 nM against ³H-spiroperidol binding in this standard test procedure.

The serotoninergic properties of the compounds of this invention were established by the procedure of Hall et al., J. Neurochem. 44, 1685–1696 (1985) by demonstrating that representative compounds exemplified herein displace ³H-8-OH DPAT (dipropylaminotetralin) from the 5-HT$_{1A}$ serotonin receptor subtype. The results of this standard pharmacological procedure are reported, infra, as the percent inhibition at 100 nM concentration of test compound or by providing the inhibition constant $K_i$ for the specific test compound where that calculation has been made from appropriate IC$_{50}$ values. Buspirone exhibits a $K_i$ value of 10 nM (97% inhibition at 1 μM) in this test procedure.

| Biological Data | | |
|---|---|---|
| | Affinity for 5-HT$_{1A}$ Receptor Sites | |
| Example | % Inhibition at 100 nM | $K_i$ in nM |
| 1 | 78% | 30 |

-continued

| | Biological Data |
|---|---|
| 2 | 47% |
| 3 | 92% |
| 4 | 72% |
| 5 | 46% |

| Example | Affinity for $D_2$ Receptor Sites<br>% Inhibition at 1 µM |
|---|---|
| 1 | 42% |
| 2 | not tested |
| 3 | 71% |
| 4 | 14% |
| 5 | not tested |

The compounds of the present invention may be administered by any route and in any appropriate manner.

Oral administration as well as parenteral administration, e.g., subcutaneous, itravenous, intramuscular or intraperitoneal injection are possible.

The dose can be determined depending on the age, condition and weight of the patient, the sorts of concurrent treatment, if any, the frequency of administration and the nature of desired effect. Generally, a daily dose of 0.5 to 50 mg/kg, usually 1 to 30 mg/kg-body weight of the active ingredient is administered in one or several doses.

For oral administration the compounds of the invention may be used in the form of tablets, capsules, powders, liquids, elixirs and the like, while for parenteral administration they are used in the form of sterilized liquids such as solutions or suspensions. When the active ingredients are formulated into the above-mentioned form, a solid or liquid, non-toxic pharmaceutical carrier may be incorporated in the formulations.

As an example of the solid carrier, conventional gelatine-type capsules are used. Also the active ingredients may be formulated into tablets or packaged powders with or without an adjuvant.

These capsules, tablets and powders generally contains 5 to 95%, preferably 25 to 90% by weight active ingredient.

Thus a dosage unit for oral administration will contain 5 to 500 mg, preferably 25 to 250 mg of the active ingredient.

As the liquid carrier, for example, water, oils such as petroleum, peanut oil, soybean oil, mineral oil and sesame oil and synthetic oils can be used. In general, preferred liquid carriers are isotonic saline solution, aqueous dextrose or similar sucrose solution, ethylene glycol, propylene glycol and polyethylene glycol.

Liquids for oral administration are preferably in the form of suspensions or syrups containing 0.5 to 10% by weight active ingredient. In that case, water-like excipients such as pharmaceutical micelles, syrups and flavoring agents can be used as carriers.

We claim:

1. The compound having the structure (I)

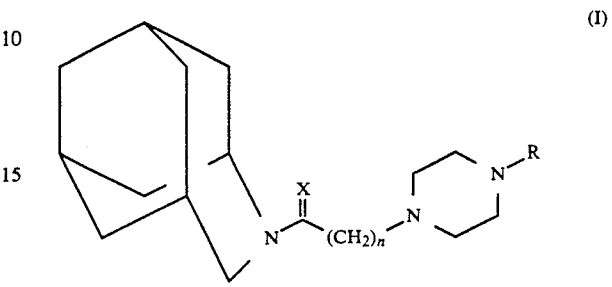

wherein R is unsubstituted or substituted phenyl, or pyrimidinyl, wherein the substituents are selected from the group consisting of lower alkyl containing 1 to 6 carbon atoms, lower alkoxy containing 1 to 6 carbon atoms, halo, cyano, nitro, and perhalomethyl; X is O or $H_2$; n is 1 to 4 or a pharmaceutically acceptable salt thereof.

2. The compound according to claim 1 wherein R is substituted phenyl wherein the substituents are selected from the group consisting of methoxy or halogen or R is pyrimidinyl; X is O or $H_2$; n is 2 or a pharmaceutically acceptable salt thereof.

3. The compound according to claim 2 1-(4-azatricyclo[4.3.1.1(3,8)]undec-4-yl)3-[4-(3-chlorophenyl)-1-piperazinyl]-1-propanone or a pharmaceutically acceptable salt thereof.

4. The compound according to claim 2 4-[3-[4-(3-chlorophenyl)-1-piperazinyl]propyl]-4-azatricyclo[4.3.1.1(3,8)]undecane or a pharmaceutically acceptable salt thereof.

5. The compound according to claim 2 1-(4-azatricyclo[4.3.1.1(3,8)]undec-4-yl)3-[4-(2-methoxyphenyl)-1-piperazinyl]-1-propanone or a pharmaceutically acceptable salt thereof.

6. The compound according to claim 2 4-[3-[4-(2-methoxyphenyl)-1-piperazinyl]propyl]-4-azatricyclo[4.3.1.1(3,8)]undecane or a pharmaceutically acceptable salt thereof.

7. The compound according to claim 2 1-(4-azatricyclo[4.3.1.1(3,8)]undec-4-yl)3-[4-(2-pyrimidinyl)-1-piperazinyl]-1-propanone or a pharmaceutically acceptable salt thereof.

* * * * *